US006927195B2

(12) United States Patent
Birch et al.

(10) Patent No.: US 6,927,195 B2
(45) Date of Patent: Aug. 9, 2005

(54) PARTICLES

(75) Inventors: Richard Arthur Birch, Kent (GB); Joseph Brain, Baarn (NL); Jeremy Nicholas Ness, Kent (GB)

(73) Assignee: Quest International Services B.V., Naarden (NL)

( * ) Notice: Subject to any disclaimer, the term of this patent is extended or adjusted under 35 U.S.C. 154(b) by 213 days.

(21) Appl. No.: 10/343,128

(22) PCT Filed: Jul. 27, 2001

(86) PCT No.: PCT/GB01/03410

§ 371 (c)(1), (2), (4) Date: Jan. 28, 2003

(87) PCT Pub. No.: WO02/09663

PCT Pub. Date: Feb. 7, 2002

(65) Prior Publication Data

US 2003/0180340 A1 Sep. 25, 2003

(30) Foreign Application Priority Data

Aug. 2, 2000 (GB) .......................................... 0018811

(51) Int. Cl.[7] .............................. C11D 3/50; A61K 7/46

(52) U.S. Cl. .......................................... 510/101; 512/4

(58) Field of Search ................................ 510/475, 476, 510/438, 441, 101; 512/4

(56) References Cited

U.S. PATENT DOCUMENTS

| | | | | |
|---|---|---|---|---|
| 5,137,646 A | * | 8/1992 | Schmidt et al. | 510/515 |
| 6,024,943 A | | 2/2000 | Ness et al. | 424/59 |
| 2001/0021404 A1 | | 9/2001 | Uhlemann et al. | 426/89 |

FOREIGN PATENT DOCUMENTS

| | | |
|---|---|---|
| EP | 0 397 246 | 11/1990 |
| WO | WO 97/11151 | 3/1997 |
| WO | 98/28339 | 7/1998 |

* cited by examiner

*Primary Examiner*—John R. Hardee
(74) *Attorney, Agent, or Firm*—Morgan, Lewis & Bockius LLP

(57) ABSTRACT

Particles suitable for inclusion in a dry product or article, typically a laundry powder, comprise a core of swellable material, e.g. an organic polymer, containing perfume absorbed therein, the core being coated with water-soluble encapsulating material impervious to the perfume. The coating of the particles acts to prevent premature evaporation or dissipation from the particles of the loaded perfume until the coating is dissolved on contact with water in use.

14 Claims, 1 Drawing Sheet

PARTICLES

FIELD OF THE INVENTION

Figure 1:
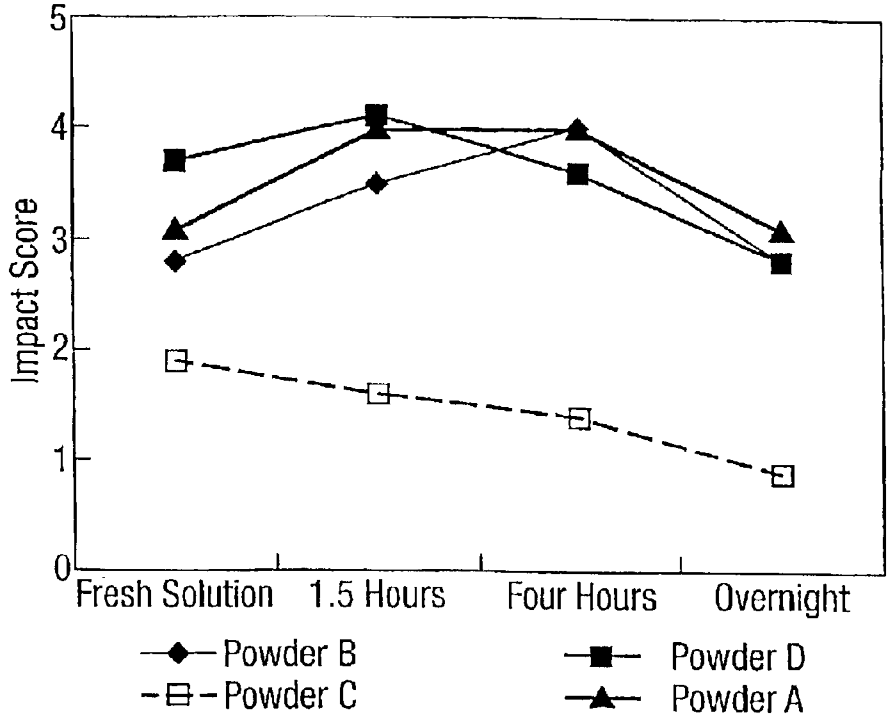

The present invention relates to particles containing a perfume absorbed therein. The particles are suitable for inclusion in a dry product or article.

BACKGROUND OF THE INVENTION

The advantages of delivering a liquid, particularly a perfume, from an encapsulate system are well documented in the literature. Some of the advantages attained by encapsulating a liquid include the enablement of controlled and/or sustained delivery of the liquid from products comprising encapsulates, the ability to enhance the stability of a liquid such as perfume and the possibility of protecting and segregating incompatible ingredients. Many different encapsulate systems and preparations thereof have been developed, which find application in numerous consumer products, such as, for example, laundry and cleaning preparations, cosmetic compositions such as creams, lotions, gels and the like and personal care preparations such as deodorants, antiperspirants and shower gels, amongst others.

WO 98/28398 describes water-insoluble particles comprising an organic polymer and imbibed liquid having a hydroxy functional polymer at the exterior of the particles. The imbibed liquid is preferably perfume, although sunscreening agents are also mentioned as a possibility. The organic polymer particles are described as solid particles (but possibly also porous solid) and the hydroxy functional polymer which may form a complete or incomplete coating on the particle is described as enhancing the deposition and/or retention of the particles on various surfaces. Further, the attachment of the hydroxy functional polymer to the particles is described such that the polymer is not completely removed upon contact with water and may be chemically bonded with the core polymer. Desirably, according to the required use, the imbibed liquid is retained in the particles and released slowly therefrom.

WO 98/28396 discloses products, such as for example, solid or liquid laundry detergent compositions, rinse conditioning liquids, or bars for personal washing, containing an active ingredient and the particles described in above-mentioned WO 98/28398.

EP-B-441,512 relates to a swellable oil-absorbent cross-linked polymer obtained by polymerising at least 90% by weight of a monomer having as its main moiety an alkyl (meth) acrylate and from 0.001 to 10% by weight of cross-linkable monomer. The cross-linked polymer is described as absorbing a wide range of oils including aromatic components.

Particles comprising polymers as hereinabove described may be effectively employed in products which are in liquid form, such as for example, rinse conditioners. In these types of products, the dynamics of the system are such, that if the absorbed or imbibed perfume of the particle is lost to the liquid carrier of the product, the lost perfume may be replaced by further perfume contained in the liquid carrier. A system may be devised, such that the equilibrium favours a high proportion of the imbibed perfume to reside in the particles thus enhancing the amount of perfume delivered to a desired surface.

However, it has been found that when such particles are employed in dry products, e.g. granular laundry powders, the particles typically demonstrate a limited useful lifetime.

If the imbibed liquid is for example perfume, the perfumery ability of the particle is lost upon storage, with the perfume evaporating or slowly being released from the particle to the atmosphere or surrounding laundry powder base. Once released, there is no mechanism in a dry product for returning the perfume to the particle. This effect is disadvantageous in products intended for use in laundry applications for example, where it is desirable to deliver fragrance to a fabric surface of an article upon washing, and a lingering and prolonged fragrance during the storage of laundered articles.

WO 98/12291 relates to a laundry additive particle suitable for use in a laundry or cleaning composition comprising a porous carrier core (into which perfume may be incorporated) encapsulated within two surface coating layers of specified materials having specified physical properties, wherein the particle has a hygroscopicity value of less than 80%. The porous carrier may be any of a number of porous solids, but is preferably a zeolite. The encapsulating materials of the first coating layer are derived from at least one partially water-soluble hydroxylic compound including for example, carbohydrates e.g. simple sugars, polysaccharides and starches, amongst others, and natural and synthetic gums. The encapsulating materials of the second coating layer are carbohydrates which optionally may include other additives.

WO 98/41607 relates to particles and compositions thereof, comprising glassy particles containing agents useful for laundry and cleaning applications, such as for example, perfume. The glassy particle comprises a glass derived from at least one partially water-soluble hydroxylic compound having specified physical properties and possibly also a perfume carrier material when the laundry and cleaning agent is perfume. Suitable perfume carrier materials include porous solids, preferably zeolites.

WO 97/47720 relates to a process for preparing a particulate laundry additive composition for perfume delivery in laundry and fabric softening products, comprising porous carrier particles loaded with perfume and encapsulated within appropriate material comprising a pigment. As per WO 98/12291 and WO 98/41607 described above, the porous carrier material is a porous solid and is preferably a zeolite.

The use of a porous carrier material in a particle such as described in the above-mentioned art may not result in the desired fragrance impact delivered to, and maintained on, laundered or cleaned articles. Porous materials such as zeolites may release perfume rapidly upon contact with water, thus reducing the amount of perfume residing in the particles upon deposition on a surface e.g. fabric surface of an article from the wash liquor or rinse.

SUMMARY OF THE INVENTION

According to a first aspect of the present invention, there is provided a particle suitable for inclusion in a dry product or article, comprising:

a core of swellable material containing perfume absorbed therein, the core being coated with at least one water-soluble encapsulating material which is impervious to the said perfume.

According to a second aspect of the present invention, there is provided a dry product or article containing a particle in accordance with the invention.

A particle in accordance with the present invention may comprise a plurality of cores of swellable material loaded with perfume within common encapsulating material, i.e. an agglomerate, and additionally, or alternatively, an individual core of swellable material loaded with perfume and coated with encapsulating material.

The particles of the present invention are impervious to the absorbed perfume by virtue of the encapsulating material which coats a core of swellable material preventing evaporation or dissipation of the loaded perfume from the particles to the atmosphere or their surroundings, e.g. laundry product base. Thus, advantageously, when the particles of the present invention are incorporated in a dry product or article, the particles remain stable upon storage with improved perfume retention. Furthermore, when the particles are incorporated into a cleaning product of dry form, e.g. laundry powder or tablet, the particles may be stable to attack by other ingredients in the product base and are typically able to withstand conditions of high relative humidity. Additionally and conveniently, particles in accordance with the invention retain substantial amounts of the absorbed perfume upon exposure to water and demonstrate excellent in-use perfume release characteristics from a laundry product during the soaking of fabric articles and/or following deposition of the particles on a fabric surface.

The term “swellable” as used herein, means a material which expands and increases in volume when in contact with a perfume, as the perfume is absorbed into the material. As a result a core of swellable material on absorption of perfume becomes swollen.

The term “non-porous” as used herein means a material which does not contain pores and/or cavities.

The term “coated” as used herein means a layer of encapsulating material which is applied to a core such that the core is in intimate contact with the encapsulating material, being fully covered and enclosed within said encapsulating material.

The term “stable” as used herein means that the integrity of a particle remains unaffected upon exposure of the particle to typical conditions of 20° C./40% relative humidity, and preferably 37° C./70% relative humidity and/or exposure of the particle to hostile agents contained in dry products or articles such as enzymes and the like, so that there is no premature release of absorbed perfume by degradation of the coating.

The term “high relative humidity” as used herein means typically 20° C./40% relative humidity, and preferably 37° C./70% relative humidity.

The term “water-soluble” as used herein means a material or mixture of materials which dissolve(s) completely in water or aqueous solutions, possibly under a variety of conditions of temperature and pH, e.g. at neutral or alkaline pH, i.e. pH 7 to 12, possibly at 40° C., preferably at 30° C., and more preferably at 20° C.

SWELLABLE CORE MATERIAL

The swellable core material comprising the particles of the present invention is typically, and preferably, non-porous and is suitably an organic polymer.

Preferably, the organic polymer produced by polymerisation results in a solid core, rather than a hollow capsule. Advantageously, formation of a solid core enables access to the desired size range of particles, and the polymerisation reaction may be carried out in the absence of perfume.

Suitable organic polymers useful herein are polymers of a vinyl monomer which may be cross-linked or partially cross-linked. It is also possible to use simple linear polymers, however, these can give cores which may lack structural integrity so may dissolve when added to a perfume, or at least be somewhat sticky. Thus, it is usually convenient and preferred to introduce some cross-linking or chain branching.

Therefore, suitable organic polymers useful herein may be formed by polymerisation of vinyl monomers, with some cross-linking and/or chain branching agent included in the monomers which are polymerised, so that some cross-links are formed between the polymer chains. If a cross-linking agent is used, the proportion of cross-linking may be low, so that after polymerisation there may be some polymer chains which remain entirely linear and are not cross-linked to any other chains.

A number of vinyl monomers containing a single carbon-carbon double bond may be used. One suitable category of monomers (A) are esters of acrylic and alkyl acrylic acids of formula:

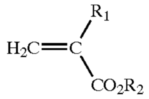

where $R_1$ is hydrogen or straight or branched alkyl of 1 to 6 carbon atoms, preferably 1 to 3 carbon atoms and $R_2$ is straight or branched alkyl of 1 to 8 carbon atoms, preferably 3 to 6 and most preferably 3 or 4 carbon atoms in a straight or branched chain.

These monomers may be used either singly, or in the form of a combination of two or more monomers.

Specific examples of suitable monomers are isobutyl methacrylate (which is particularly preferred), n-butyl acrylate, n-butyl methacrylate, isobutyl acrylate, n-propyl acrylate and iso-propylmethacrylate. Less preferred is methyl methacrylate.

Another suitable monomer is styrene.

Cross-linking between polymer chains formed from the above monomers can be achieved by including in the monomer mixture a small proportion—for example less than 10%, preferably as little as 5% or 1%—of a monomer having at least two carbon-carbon double bonds. The use of such a material to provide cross-linking is well known in other applications of polymers, although it is usual to introduce a greater proportion of cross-linking than is required for this invention. Examples of this type of cross-linking agent are divinyl benzene, diesters formed between acrylic acid and diols, such as 1,4-butane diol diacrylate, and higher esters formed between acrylic acid and polyols—which may be sugars.

Chain branching can be introduced by including among the monomers a hydroxyalkyl monomer of formula:

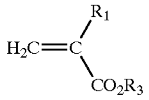

where $R_1$ is as specified above and $R_3$ is alkyl of 1 to 6 carbon atoms bearing at least one hydroxy group, preferably 3 to 4 carbon atoms in a straight or branched chain and bearing a single hydroxy group. These monomers undergo a side reaction during the course of polymerisation, and this side reaction produces chain branching. When there is chain branching without cross-linking, it is suitable that a hydroxyalkyl monomer of the above formula provides from 10 to 40% by weight of the monomer mixture.

Suitable hydroxyalkyl monomers are hydroxypropyl methacrylate, hydroxybutylacrylate, and hydroxyethylacrylate.

A further suitable category of monomers (B) are esters of acrylic or methacrylic acids of formula:

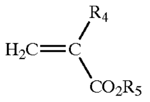

where $R_4$ is hydrogen or methyl and $R_5$ is a straight or branched alkyl of 9 to 16 carbon atoms.

These monomers may be used either singly, or in the form of a combination of two or more monomers.

Specific examples of suitable monomers of the aforementioned category include decyl (meth)acrylates, dodecyl (meth)acrylates, tetradecyl (meth)acrylates, and hexa-decyl (meth)acrylates.

The above-described monomers of category (B) may be combined with one or more further monomers which possess a polymerising unsaturated group, provided that the monomers of category (B) account for the main moiety and are present in not less than 50% by weight of the monomer mixture.

The further monomers which are effectively usable in combination with the monomers of category (B) include (meth)acrylates of monovalent aliphatic alcohols of not more than 9 carbon atoms such as methyl (meth)acrylates, ethyl (meth)acrylates, butyl (meth)acrylates, 2-ethylhexyl (meth)acrylates, and n-octyl (meth)acrylates; (meth) acrylates of monovalent aliphatic alcohols of not less than 17 carbon atoms such as octadecyl (meth)acrylates and behenyl (meth)acrylates; (meth)acrylates of alicyclic alcohols such as cyclo-hexyl (meth)acrylates and menthyl (meth)acrylates; (meth)acrylates of phenols such as phenyl (meth)acrylates and octylphenyl (meth)acrylates; aminoalkyl (meth)acrylates such as dimethylaminoethyl (meth) acrylates and diethylaminoethyl (meth)acrylates; (meth) acrylates possessing a polyoxyethylene chain such as polyethylene glycol mono(meth)acrylates and methoxy-polyethylene glycol mono(meth)acrylates; (meth) acrylamides such as (meth)acrylamides, N-methylol (meth) acrylamides, and dimethylaminoethyl (meth)acrylamides; polyolefins such as ethylene and propylene; aromatic vinyl compounds such as styrene, α-methyl styrene, and t-butyl styrene; and vinyl chloride, vinyl acetate, acrylonitrile, and (meth)acrylic acids, for example. These monomers may be used either singly, or in the form of a combination of two or more monomers.

Cross-linking between polymer chains formed from the above-mentioned monomers can be achieved by including greater than 0.001% to less than 10% by weight of a cross-linkable monomer having at least two carbon-carbon double bonds which functions as a cross-linking agent.

Examples of suitable cross-linkable monomers for use with category (B) monomers include ethylene glycol di(meth)acrylates, diethylene glycol di(meth)acrylates, polyethylene glycol di(meth)acrylates, polyethylene glycol polypropylene glycol di(meth)acrylates, polypropylene glycol di(meth)acrylates, 1,3-butylene glycol di(meth) acrylates, N,N-propylene bis-acrylamide, diacrylamide dimethyl ether, N,N-methylene bis-acrylamide, glycerol di(meth)acrylates, neopentyl glycerol di(meth)acrylates, 1,6-hexane diol di(meth)acrylates, trimethylol propane tri (meth)acrylates, tetramethylol propane tetra(meth)acrylates, polyfunctional(meth)acrylates obtained by the esterification of alkylene oxide adducts of polyhydric alcohols (such as, for example, glycerine, neopentyl glycol, trimethylol propane, trimethylol ethane, and tetramethylol methane) with (meth)acrylic acids, and divinyl benzene, for example. These cross-linkable monomers may be used either singly, or in the form of a combination of two or more monomers.

The properties of the resulting cross-linked polymers obtained by reacting monomers of category (B) with a suitable cross-linkable monomer (or an optional further monomer as above described) and methods for their preparation, are described more fully in EP-B-441,512, incorporated herein by reference.

Optionally, a particle as described herein may additionally comprise at the exterior of the core, a further polymer which incorporates free hydroxyl groups, as described more completely in WO 98/28398, incorporated herein by reference. Advantageously, the attachment of the polymer incorporating free hydroxyl groups to the core is such that the polymer is not completely removed upon contact of the particle with water. Therefore, under the appropriate conditions, the water-soluble encapsulating material typically dissolves and the polymer incorporating free hydroxyl groups serves to enhance deposition onto (or retention on) skin or surfaces such as vitreous surfaces or fabric. Typically, the further polymer which incorporates free hydroxyl groups is selected from polyvinyl alcohol, cellulose, or chemically modified cellulose.

Organic polymers comprising a monomer from either category (A) or (B) may be prepared using the technique of suspension polymerisation. This is a process in which the organic monomers are formed into a suspension in an aqueous phase, and polymerised. It is customary to stabilise the suspension by incorporating a stabilising agent in the aqueous phase before adding one or more monomers. Suitable stabilising agents include polyvinyl alcohol, anionic surfactants, or non-ionic surfactants with HLB of at least 8. Alternatively, the organic polymers may be formed by emulsion polymerisation which technique produces cores of approximately <1 μm which can be agglomerated to a desired particle size. Polymerisation of each suspended droplet leads to a bead of polymer. These techniques are more fully described in WO 98/28398, herein incorporated by reference.

A further suitable technique for the preparation of organic polymers includes bulk or solvent polymerisation which technique produces blocks of polymers which may require grinding to particulate form.

If the particle comprises a further polymer with free hydroxyl groups, such as polyvinyl alcohol, at the exterior of a core, attachment of said further polymer can be achieved by polymerising the monomers in the presence of the polymer with free hydroxyl groups using the technique of suspension polymerisation as described in WO 98/28398.

Perfume

As used herein the term "perfume" denotes a substantially water-insoluble composition of matter consisting of one or more perfume components, optionally mixed with a suitable solvent or diluent, which is used to impart a desired odour to the product to which it is added and/or to skin or fabric. Perfume components are those constituents of a perfume which are added thereto only or primarily for their olfactive contribution. The number of perfume components in a perfume is typically ten or more. In many instances, the molecular weight of a perfume component is in excess of 150, but does not exceed 300.

Perfume components may be natural products such as essential oils, absolutes, resinoids, resins, concretes, etc., and synthetic perfume components such as hydrocarbons, alcohols, aldehydes, ketones, ethers, acids, esters, acetals, ketals, nitriles, etc., including saturated and unsaturated aliphatic, carbocyclic and heterocyclic compounds.

The particles of the present invention typically comprise from 5% to 50% by weight of the particle of perfume, preferably from 10% to 40%, and more preferably from 15% to 30%.

Perfume components which may be used in the particles of the present invention include: acetyl cedrene, 4-acetoxy-3-pentyltetrahydropyran, 4-acetyl-6-t-butyl-1,1-dimethylinidane, available under the trade mark "CELESTOLIDE", 5-acetyl-1,1,2,3,3,6-hexamethylindane, available under the trademark "PHANTOLIDE", 6-acetyl-1-isopropyl-2,3,3,5-tetramethylindane, available under the trade mark "TRASEOLIDE", alpha-n-amylcinnamic aldehyde, amyl salicylate, aubepine, aubepine nitrile, aurantion, 2-t-butylcyclohexyl acetate, 2-t-butylcyclohexanol, 3-(p-t-butylphenyl) propanal, 4-t-butylcyclohexyl acetate, 4-t-butyl-3,5-dinitro-2,6-dimethyl acetophenone, 4-t-butylcyclohexanol, benzoin siam resinoids, benzyl benzoate, benzyl acetate, benzyl propionate, benzyl salicylate, benzyl isoamyl ether, benzyl alcohol, bergamot oil, bornyl acetate, butyl salicylate, carvacrol, cedar atlas oil, cedryl methyl ether, cedryl acetate, cinnamic alcohol, cinnamyl propionate, cis-3-hexenol, cis-3-hexenyl salicylate, citronella oil, citronellol, citronellonitrile, citronellyl acetate, citronellyloxyacetaldehyde, cloveleaf oil, coumarin, 9-decen-1-ol, n-decanal, n-dodecanal, decanol, decyl acetate, diethyl phthalate, dihydromyrcenol, dihydromyrcenyl formate, dihydromyrcenyl acetate, dihydroterpinyl acetate, dimethylbenzyl carbinyl acetate, dimethylbenzylcarbinol, dimethylheptanol, dimethyloctanol, dimyrcetol, diphenyl oxide, ethyl naphthyl ether, ethyl vanillin, ethylene brassylate, eugenol, geraniol, geranium oil, geranonitrile, geranyl nitrile, geranyl acetate, 1,1,2,4,4,7-hexamethyl-6-acetyl-1,2,3,4-tetrahydronaphthalene, available under the trademark "TONALID", 1,3,4,6,7,8-hexahydro-4,6,6,7,8,8-hexamethylcyclopenta-2-benzopyran, available under the trade mark "GALAXOLIDE", 2-n-heptylcyclopentanone, 3a,4,5,6,7,7a-hexahydro-4,7-methano-1(3)H-inden-6-ylpro available under the trade mark "FLOROCYCLENE", 3a,4,5,6,7,7a-hexahydro-4,7-methano-1(3)H-inden-6-ylac available under the trade mark "JASMACYCLENE", 4-(4'-hydroxy-4'-methylpentyl)-3-cyclohexenecarbaldehyde, alpha-hexylcinammic aldehyde, heliotropin, HERCOLYN D, which is a trade mark of Hercules Inc. and is a mixture of dihydro and tetrahydro methyl abietate, hexyl aldone, hexyl cinnamic aldehyde, hexyl salicylate, hydroxycitronellal, i-nonyl formate, 3-isocamphylcyclohexanol, 4-isopropylcyclohexanol, 4-isopropylcyclohexyl methanol, indole, ionones, irones, isoamyl salicylate, isoborneol, isobornyl acetate, isobutyl salicylate, isobutylbenzoate, isobutylphenyl acetate, isoeugenol, isolongifolanone, isomethyl ionones, isononanol, isononyl acetate, isopulegol, lavandin oil, lemongrass oil, linalool, linalyl acetate, methyl beta orcinyl carboxylate (LRG 201), 1-menthol, 2-methyl-3-(p-isopropylphenyl)propanal, 2-methyl-3-(p-t-butylphenyl) propanal; 3-methyl-2-pentyl-cyclopentanone, 3-methyl-5-phenyl-pentanol, alpha and beta methyl naphthyl ketones, methyl ionones, methyl dihydrojasmonate, methyl naphthyl ether, methyl 4-propyl phenyl ether, Mousse de chene Yugo, myrtenol, neroli oil, nonanediol-1,3-diacetate, nonanol, nonanolide-1,4, nopol acetate, 1,2,3,4,5,6,7,8-octahydro-2,3,8,8-tetramethyl-2-acetyl-naphthalene, available under the trade mark "ISO-E-SUPER", octanol, Oppoponax resinoid, orange oil, p-t-amylcyclohexanone, p-t-butylmethylhydrocinnamic aldehyde, 2-phenylethanol, 2-phenylethyl acetate, 2-phenylpropanol, 3-phenylpropanol, para-methan-7-ol, para-t-butylphenyl methyl ether, patchouli oil, pelargene, petitgrain oil, phenoxyethyl isobutyrate, phenylacetaldehyde diethyl acetal, phenylacetaldehyde dimethyl acetal, phenylethyl n-butyl ether, phenylethyl isoamyl ether, phenylethylphenyl acetate, pimento leaf oil, rose-d-oxide, Sandalone, styrallyl acetate, 3,3,5-trimethyl hexyl acetate, 3,5,5-trimethylcyclohexanol, terpineol, terpinyl acetate, tetrahydrogeraniol, tetrahydrolinalool, tetrahydromuguol, tetrahydromyrcenol, thyme oil, trichloromethylphenylcarbinyl acetate, tricyclodecenyl acetate, tricyclodecenyl propionate, 10-undecen-1-al, gamma undecalactone, 10-undecen-1-ol, undecanol, vanillin, vetiverol, vetiveryl acetate, vetyvert oil, acetate and propionate esters of alcohols in the list above, aromatic nitromusk fragrances, indane musk fragrances, isochroman musk fragrances, macrocyclic ketones, macrolactone musk fragrances, and tetralin musk fragrances.

Perfumes frequently include solvents or diluents, for example: ethanol, isopropanol, diethylene glycol monoethyl ether, dipropylene glycol, diethyl phthalate and triethyl citrate.

Perfumes which are used in this invention may, if desired, have deodorant properties as disclosed in U.S. Pat. No. 4,303,679, U.S. Pat. No. 4,663,068 and EP-A-545556.

If the cores are impregnated with a perfume after manufacture, we have found that the absorption of perfume can be enhanced by choosing materials with a hydrophobic character, or by mixing a hydrophobic oil into the perfume.

Examples of hydrophobic oils which can enhance perfume uptake include dibutyl phthalate and alkane mixtures such as isoparaffin and di($C_8$–$C_{10}$ alkyl) propylene glycol diesters.

When the cores of swellable material as described hereinabove are allowed to absorb a perfume, they can absorb a surprising quantity, typically at least their own weight of perfume and often in excess of their own weight.

Typically, the w/w ratio of core material to perfume is in the range 5:1 to 1:5, preferably in the range 3:1 to 1:5 and more preferably in the range 2:1 to 1:5.

Incorporation of Perfume in a Core of Swellable Material

The absorption of a perfume by a core of swellable material, can be brought about by simply bringing the perfume and the core into contact, and allowing them to stand. This may be achieved by mixing a perfume with the cores after they have been separated from the aqueous phase, or it may be achieved by mixing perfume into an aqueous slurry of cores and allowing the mixture to equilibrate. It can also be achieved by mixing the core and perfume separately into an aqueous liquid product and allowing that mixture to equilibrate.

Encapsulating Material

The particles of the present invention comprise a water-soluble encapsulating material which is impervious to perfume.

The term "water-soluble encapsulating material" as used herein is intended to cover one, or a mixture of materials. For brevity and simplicity, the water-soluble encapsulating material will be referred to as "the encapsulating material" or "the encapsulating materials" or "an encapsulating material".

Typically, the encapsulating materials useful herein are capable of forming a uniform, cohesive coating around a core of swellable material, thus conveniently enabling retention of the absorbed perfume within the particle. Furthermore, art encapsulating material completely dissolves upon contact of the particles with water or aqueous solutions at neutral or alkaline pH as it is not chemically bonded to a core. The encapsulating material is also suitably stable under conditions of high relative humidity (being substantially non-hygroscopic). Additionally, or alternatively, the encapsulating material may be stable to attack by hostile ingredients in a dry product or article.

Preferably, the encapsulating material suitable for use herein forms a glassy ie. non crystalline coating. The glass is formed by heating the material to above the glass transition temperature, Tg, of the material. Alternatively, in order to facilitate processing, the material may be heated to above its melting temperature, Tm.

The water-soluble encapsulating materials useful herein are generally selected from hydroxylic compounds, proteins, and synthetic film-forming polymers, or mixtures thereof. Preferably, the water-soluble encapsulating materials are hydroxylic compounds or synthetic film-forming polymers, and mixtures thereof.

Suitable hydroxylic compounds for use herein are typically selected from one or more of carbohydrates, or derivatives thereof, and natural or synthetic gums, or mixtures thereof. Preferably, the hydroxylic compound is a carbohydrate, or derivative thereof.

Suitable carbohydrates, or derivatives thereof for use herein can be any or a mixture of a: i) sugar where in the context of the invention the term "sugar" is intended to cover monosaccharides, disaccharides, oligosaccharides, polysaccharides and polyols and derivatives thereof and references to "sugar" should be construed accordingly; ii) starches including modified starches and hydrolysates; and iii) hydrogenates of i) and ii), e.g. maltodextrin.

Both linear and branched carbohydrate chains may be used. In addition chemically modified starches may be used. Typical modifications include the addition of hydrophobic moieties of the form of alkyl or aryl groups etc., identical to those found in surfactants to impart some surface activity to these compounds. Preferred carbohydrates, or derivatives thereof for use herein are sugars, starches or modified starches, and mixtures thereof, possibly admixed with hydrogenates of sugars and starches e.g. maltodextrin available for example under the trade name "Glucidex 21" from Roquette Freres, Lestrem, France.

Suitable sugars for use herein include sucrose, maltose, mannitol, maltitol and anhydrous isomalt, or mixtures thereof.

A preferred sugar is maltose, available for example as a maltose syrup under the trade name "Flolys D5780" from Roquettes Freres or as a high maltose syrup under the trade name "Flolys D5777S" which also contains other mono, oligo and polysaccharides and is also commercially available from Roquette Freres, Lestrem, France.

Suitable starches or modified starches include Capsul E™, N-LOK™ and Hi-Cap™, all of which are commercially available from National Starch Chemical Co., Bridgewater, USA.

Examples of suitable natural or synthetic gums for use herein include alginic acid and salts and derivatives thereof, carrageenan, xanthan gum, carboxymethyl cellulose salts, gum arabic, gum tragacanth and gum karaya.

Proteins suitable for the purposes of the present invention include for example, gelatin and casein, and derivatives thereof.

Also suitable for use herein are synthetic film-forming polymers where in the context of the invention, by the term "film-forming" is meant a polymer which is capable of forming a coherent coating. Generally, synthetic film-forming polymers having a carboxylic acid moiety are insoluble at acidic pH but are typically water-soluble under the in-use conditions of a cleaning product, i.e. at alkaline pH. Examples of suitable synthetic film-forming polymers include polyacrylic acid based polymers, such as for example the Glascol™ series commercially available from Ciba Speciality Chemicals, Bradford, UK, which are polymer latices of polyacrylic acid; polymethacrylic acid based polymers such as the Eudragit™ series commercially available from Rohm & Haas, Philadelphia, USA; polyacrylonitrile; and polyvinyl alcohol commercially available for example as Gohsenol GH-23™ from Nippon Gohsei, Osaka, Japan, with polyvinyl alcohols having a high amount of hydrolysis being preferred.

Glass transition temperature, commonly abbreviated "Tg", is a well known and readily determined property for glassy materials. This transition is described as being equivalent to the liquidification, upon heating through the Tg region, of a material in the glassy state to one in the liquid state. It is not a phase transition such as melting, vaporization, or sublimation. [See William P. Brennan, "What is a Tg?" A review of the scanning calorimetry of the glass transition", *Thermal Analysis Application Study #7*, Perkin-Elmer Corporation, March 1973.] Measurement of Tg is readily obtained by using a Differential Scanning Calorimeter.

For the purposes of the present invention, the Tg of a water-soluble encapsulating material is obtained for the anhydrous material not containing any plasticizer (which will impact the measured Tg value of the water-soluble encapsulating material). Glass transition temperature is also described in detail in P. Peyser, "Glass Transition Temperatures of Polymers", *Polymer Handbook, Third Edition*, J. Brandrup and E. H. Immergut (Wiley-Interscience; 1989), pp. VI/209 –VI/277.

At least one of the water-soluble encapsulating materials useful in the particles of the present invention preferably has an anhydrous, nonplasticized Tg of at least 0° C., preferably at, least about 20° C., more preferably at least about 40° C., even more preferably at least 60° C., and most preferably at least about 100° C. It is also preferred that, these materials be low temperature processable, preferably within the range of from about 50° C. to about 200° C., and more preferably within the range of from about 60° C. to about 180° C. Such water-soluble encapsulating materials include hydroxylic compounds such as sucrose, maltose, starch hydrolysates such as corn syrups and maltodextrin, and hydrogenated starch hydrolysates.

The particles of the present invention typically comprise at least about 40% by weight of the particle of a water-soluble encapsulating material, preferably at least about 50%, and more preferably at least about 60%.

The encapsulating material may include optional additive ingredients such as plasticizers, anti-agglomeration agents, pigments, dyes, preservatives, optical brighteners, pearlescent agents, salts, dispersion aids, conditioning agents and mixtures thereof.

Examples of suitable optional plasticizers include sorbitol, water, polyethylene glycol, propylene glycol, low molecular weight carbohydrates, and the like, with sorbitol, polyethylene glycol, low molecular weight polyols or water, and mixtures thereof, being preferred. Most preferred is water. Whilst not wishing to be bound by theory, it is believed that the presence of a small amount of a plasticizer in the encapsulating material helps to prevent excessive brittleness and thus cracking of the glassy coating formed around a core. The plasticizer is generally employed at levels of from about 0.01% to about 25% by weight of the encapsulating material.

Typically, if water is employed as a plasticizer in the encapsulating material, then the encapsulating material generally comprises greater than 0%, preferably greater than 1%, more preferably greater than 2%, and generally less than 10%, preferably less than 7% and more preferably less than 5% by weight of the particle of water.

The optional anti-agglomeration agents according to the present invention are preferably a surfactant and are typically included at low levels of less than 1% by weight of the encapsulating material.

Preparation of Particles

The particles described herein may be prepared using a number of techniques with the most appropriate technique being typically determined according to the nature of the encapsulating material.

A suitable technique for the preparation of particles herein is spray-drying as described in GB 1,464,616, which is incorporated herein by reference. This technique is useful for example when the encapsulating material comprises a starch (including modified starch or hydrosylates thereof). Usually, to prepare particles by spray-drying, an emulsion of cores of swellable material comprising absorbed perfume is formed in an aqueous solution of the encapsulating materials. In order to attain good results, it is preferable to have as small a droplet size of encapsulating material as possible in this emulsion (typically <5 $\mu$m) so that the resultant spray-dried particles have a coating comprising a multitude of these droplets around a core material. Typically, spray-dried particles produced by this technique are generally smaller than the desired particle size. This is because conventional spray-drying equipment is set up to produce a particle size so that satisfactory drying of the coating takes place (smaller droplets have a larger surface area and therefore take a proportionally shorter time to dry compared with large particles for which a larger spray drier would be required). Additionally, employing conventional spray-drying equipment may also facilitate ensuring that the droplets of encapsulating material stay in contact with a core material during the drying process. The spray dried particles so formed, may be agglomerated if desired in a fluidiser using methods well known in the industry. For example, the particles may be maintained in continuous motion in air in the fluidiser with a small amount of moisture being introduced. The moisture causes the surface of the particles to become sticky, facilitating their adhesion to neighbouring particles and thus agglomeration.

A further suitable and preferred technique for the preparation of particles when the encapsulating material comprises a sugar is sugar-coating. Employing this technique, the cores of swellable material are encapsulated within a glass coating of the sugar encapsulating material. Typically, the technique involves mixing the core materials with perfume absorbed therein into a syrup of sugars (typically non-hygroscopic mixtures of disaccharides and polysaccharides heated to above the melting point of the sugars), forming the finished particle by coating the said core materials with the sugar mixture and then de-hydrating at elevated temperature to form the glassy sugar coating. In a suitably devised laboratory method, core materials with perfume absorbed therein are encapsulated by simply squeezing a drop of the sugar syrup slurry out of a pipette or syringe over the said core materials to form particles in accordance with the invention. Particles as described herein may also be commercially prepared by any of extrusion, spray chilling or spinning disc techniques.

When particles as described herein are prepared by extrusion, cores of swellable material coated with molten sugar encapsulating material, are forced (usually by a rotating screw drive) through a die having one or more holes of the required size. In this manner, a 'worm' of material may be produced which can be broken up into small pieces to give particles of the desired size. Alternatively, a cutting blade may be positioned at the face of the die to cut the extruded material as it is forced out of the die to give particles of a desired size. It is common in the flavour industry to extrude into a solvent bath to remove surface oil, but this is not essential for the preparation of particles according to the present invention. The extruder may also have to remove excess water from the slurry and so a venting arrangement may be used. Extrusion is typically carried out above the Tg of the encapsulating materials but not necessarily above the Tm.

When particles in accordance with the invention are prepared by spray chilling, a melt of the encapsulating materials having an appropriate water content is produced with cores comprising absorbed perfume dispersed therein. Droplets of said core materials coated with encapsulating material are formed and then rapidly chilled to form particles as described in accordance with the present invention.

The aforementioned droplets can be formed in a variety of ways, e.g. via a spray nozzle. Additionally, or alternatively, droplets may also be formed using a 'spinning disc' where the melt is spun off the edge of a disc specially designed to form particles of the correct size.

Further suitable techniques for preparing particles useful herein include forming a slurry comprising molten sugar, water and core materials containing absorbed perfume, followed by dehydration of the slurry with a water-absorbing material (e.g. silica, sodium tripolyphosphate) at elevated temperature (to allow the glassy phase to form), the water-absorbing material and water will comprise part of the particles; dropping techniques where the (molten) encapsulating material is applied around the core materials containing absorbed perfume from concentric tubes and the encapsulating material is then hardened by cooling; crystallisation of the encapsulating material around the cores containing absorbed perfume therein; and coating the core materials containing absorbed perfume by spraying in a fluidiser.

Particle Size

Particles according to the present invention typically have an average particle size in the range from 10 micrometers to 2000 micrometers, preferably from 50 micrometers to 1500 micrometers, more preferably from 75 micrometers to 1000 micrometers and even more preferably from 100 micrometers to 750 micrometers, depending upon the type of product into which they are to be incorporated.

For example, if the particles are intended to be used in a laundry powder, it is especially preferred to use particles with an average particle size of at least 60 micrometers and desirably not larger than 2000 micrometers in order to prevent the particles segregating within the powder. However, particles having an average particle size of greater than 2000 micrometers could suitably be employed in tablets for laundry or autodishwash applications, where a single particle may comprise each tablet, delivering a single dose of perfume.

Perfume Release

The encapsulating material of the particles of the present invention, remains substantially intact upon storage and/or is conveniently resistant to degradation when the particles are employed in a dry product or article. Depending on the nature of the encapsulating material, when the particles are brought into contact with water e.g. at neutral or alkaline pH, the encapsulating material dissolves. Conveniently particles in accordance with the present invention are typically able to retain at least 60%, preferably at least 70%, and more preferably at least 80% of the absorbed perfume upon contact with water itself, i.e. without surfactants or emulsifiers dispersed therein. If the particles comprise an optional further polymer which incorporates free hydroxyl groups at the exterior of the core, then after deposition of the particles onto a surface such as a fabric surface, the perfume will be released from the deposited particle by evaporation. Alternatively, if the particles do not comprise a deposition assisting hydroxy functional polymer, perfume is slowly released from the particles into the atmosphere from an aqueous wash liquor.

Advantageously, it has been observed that upon soaking fabric articles in an aqueous liquid comprising particles of the present invention, the perfume is released slowly from the particles over an extended period of time. It is believed that the particles float to the surface of the aqueous wash liquid (being less dense) and that the perfume is slowly released from the particles forming perfume droplets on the surface of the wash liquid, resulting in a strong head space smell. The particles are too small to be visible to the naked eye, however, by incorporating a dye into the said particles it is possible to observe the dyed particles floating on the surface of the wash liquor. Whilst not wishing to be bound by theory, it is thought that the perfume released by the floating particles on the aqueous wash liquor encounters reduced attack by components of the laundry product such as surfactants and enzymes. Thus, particles in accordance with the invention advantageously demonstrate improved perfume performance during soaking.

In a further aspect, the present invention provides a process for improving perfume performance during soak from a dry laundry product comprising particles in accordance with the present invention.

Particles in accordance with the invention may be incorporated into a dry product or article e.g. selected from laundry products, such as granular laundry powders and laundry tablets, autodishwash powders, autodishwash tablets, sheet conditioners, rim blocks, soap, and powder and granular cleaning compositions.

Figure 2:
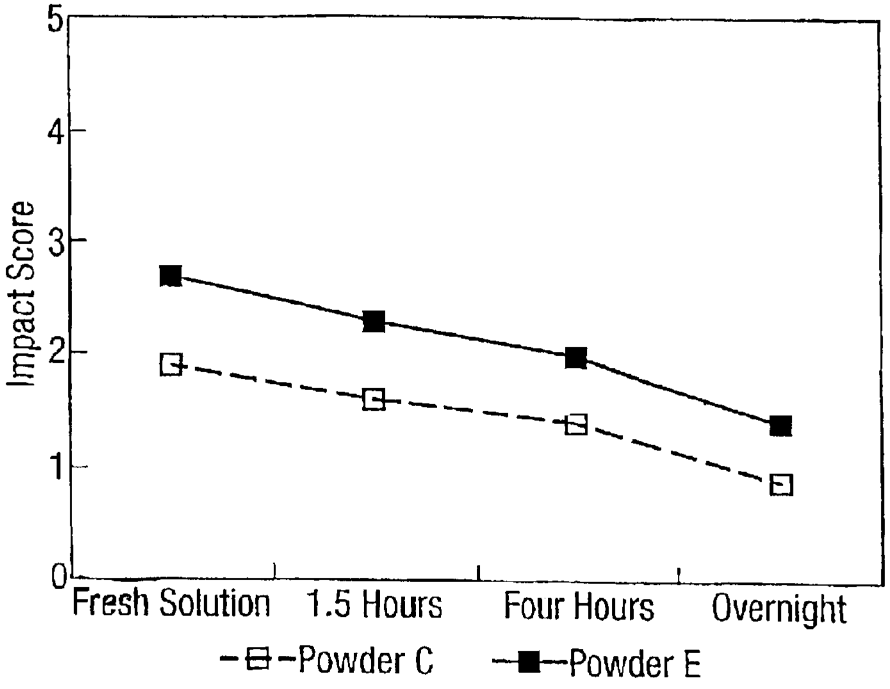

The invention is illustrated by the following non-limiting examples and with reference to the accompanying drawings, in which FIGS. 1 and 2 are graphs of perfume performance represented by impact scores with time.

All percentages are by weight unless otherwise indicated.

Preparation of Premixes A and B of Organic Polymer Containing Absorbed Perfume

A core of organic polymer was prepared as described in Examples 1 and 2 of WO 98/28398 using the standard suspension polymerisation technique, as a 37% active slurry (in water) of polyisobutylmethacrylate cross-linked with 0.5% 1,4-butane diol diacrylate (BDDA) using 88% hydrolysed polyvinyl alcohol (Gohsenol GH-23™ available from Nippon Gohsei, Osaka, Japan) as the suspension stabiliser. The resulting polymer had a mean particle size of ~85 μm.

To the resulting polymer slurry, Perfume A (a volatile orange perfume having a formulation as indicated below) was added to produce 100 g samples of each of premixes A and B.

| Perfume A (all values are by wt %) | |
|---|---|
| Octanal | 1.40 |
| Decanal | 4.40 |
| Undecylenic aldehyde | 0.50 |
| Dodecanal | 1.10 |
| Allyl Heptanoate | 5.50 |
| cis-3-hexenol | 1.40 |
| cis-3-hexenyl acetate | 1.40 |
| Citronellol | 2.00 |
| Damascone beta | 0.24 |
| Dihydromyrcenol | 2.20 |
| Dipropylene glycol | 5.24 |
| Ethyl acetate | 2.60 |
| Ethyl butyrate | 2.60 |
| Hexyl butyrate | 2.20 |
| Inonyl acetate | 2.80 |
| Isocyclo citral | 0.22 |
| Ligustral* | 0.80 |
| Manzanate* | 1.00 |
| Orange Brazilian | 44.00 |
| Ortholate* | 17.00 |
| Prenyl acetate | 1.40 |

*are trade marks of Quest International

The premixes were then allowed to stand overnight to allow the perfume to be fully incorporated into the organic polymer. The premixes had the following basic compositions:

| Premix | A | B |
|---|---|---|
| Core Organic Polymer | 27% | 13% |
| Perfume A | 27% | 65% |
| Water etc.* | 46% | 22% |

*the water also contains small amounts of residual polyvinyl alcohol, monomers etc.

These premixes were then used as prepared in the following examples.

EXAMPLE 1

Spray-Dried Particles

The following emulsion was prepared by mixing the ingredients at room temperature in the order below:

| | |
|---|---|
| Encapsulating Materials | |
| Water | 47.0% |
| Xanthan Gum[1] | 0.2% |
| Capsul E ™[2] | 14.1% |
| Sorbitol[3] | 3.5% |
| Core | |
| Premix A | 35.2% |

[1]available from ISP Corporation, Tadworth, UK.
[2]available from National Starch Chemical Co., Bridgewater, USA.
[3]available as Sorbitol Powder from Roquette Freres, Lestrem, France.

This mixture was then spray-dried on a 2.5 m diameter spray-drier (S5 machine at Drytec Ltd, Tonbridge) using a 17.78 cm (7 inch) diameter cup disc rotary atomiser operating under standard spray-drying methods and conditions (ie. disc speed 18,000 rpm, inlet temperature 220° C., outlet temperature 90° C.). The resulting particles were in the form of a free-flowing dry powder comprising a core of organic polymer with perfume absorbed therein, the core being coated with a thin layer of the encapsulating materials.

EXAMPLE 2

Sugar Coated Particles (Drop Method)

Premix A detailed above was stirred into a maltose-based syrup, Flolys D5777S (81% solids, available from Roquette Freres) to generate the following slurry:

| | |
|---|---|
| Premix A | 50% |
| Flolys D5777S | 50% |

The resulting viscous slurry was then taken up in a plastic pipette and dropped onto a heatproof surface to form droplets of approximate mass 0.05 g. The droplets were then transferred to an oven which was heated to 110° C. and allowed to dry for approximately two hours. Drying at this temperature (ie. above the melting point of the sugars in the syrup) caused the formation of an even, coherent glass around the cores of the premix, thus providing an effective barrier to perfume egress. The particles so produced had a perfume level of 12.5%.

EXAMPLE 3

Sugar Coated Particles (Drop Method)

Further particles were prepared according to the method described in Example 2 in the following quantities:

| | |
|---|---|
| Premix B | 33.33% |
| Flolys D5777S | 66.67% |

The particles produced had a perfume level of 17.5%.

EXAMPLE 4

Sugar Coated Particles with Polymer Latex (Drop Method)

Particles in accordance with the invention were prepared using the method described in Example 2 using the following composition:

| | |
|---|---|
| Premix B | 27% |
| Flolys D5777S | 27% |
| Glascol LE15 ™[4] | 46% |

4. A polyacrylate latex, available from Ciba Speciality Chemicals, Bradford, UK.

The particles so produced had a perfume level of 16.7%.

EXAMPLE 5

Sugar Coated Particles (Extrusion)

The slurry of Example 2 was used to produce pellets on a Modula Co-Rotating Twin Screw System extruder (Model TSE 24HC, Prism Ltd, Lichfield, UK), operating at 110° C. with venting to allow removal of excess water from the slurry. The pellets were produced by extrusion through a 1 mm die, a blade cutting system being used at the exit hole of the extruder to produce particles in the form of pellets. The particles produced contained 17.8% perfume and were dry to the touch and free flowing.

EXAMPLE 6

Dehydration Method

The following slurry was prepared by simple mixing in a paddle mixer:

| | |
|---|---|
| Premix B | 40% |
| Glascol LE15 ™ | 40% |
| Water | 20% |

The slurry was then transferred to a food blender fitted with a blade mixer, and an equal weight of anhydrous sodium tripolyphosphate (STPP) powder was stirred into the slurry until all of the excess water had been absorbed and a free flowing powder was produced. The particles produced by this method contained 12.8% perfume.

EXAMPLE 7

Improved Soak Performance with Sugar Coated Particles

Particles in accordance with the invention may be employed with good effect in a laundry powder as indicated below.

The following laundry powders were prepared by standard (non-tower) mixing techniques:

| | Powder A | Powder B | Powder C | Powder D |
|---|---|---|---|---|
| Sodium tripolyphosphate | 40.00 | 40.00 | 40.00 | 40.00 |
| Sodium silicate | 6.20 | 6.20 | 6.20 | 6.20 |
| Sodium sulphate | 36.85 | 36.97 | 37.20 | 36.95 |
| SDBS* | 9.00 | 9.00 | 9.00 | 9.00 |
| $C_{12-15}$ alcohol (7EO) ethoxylate | 4.30 | 4.30 | 4.30 | 4.30 |
| CMC**, enzymes, fluorescer | 3.00 | 3.00 | 3.00 | 3.00 |
| Perfume A*** | — | — | 0.05 | — |
| Perfume B**** | 0.25 | 0.25 | 0.25 | 0.25 |
| Particles of Example 2 | 0.40 | — | — | — |
| Particles of Example 3 | — | 0.28 | — | — |
| Particles of Example 4 | — | — | — | 0.30 |

*Sodium dodecyl benzene sulphonate
**Sodium carboxymethyl cellulose
***having a formulation as indicated herein above in the procedure for the preparation of Premixes A and B of organic polymer containing absorbed perfume.
****having a formulation as described in Example 8 below.

Powders A to D were then stored under "dry" conditions in standard packaging at 45° C. for one month (it will be appreciated however by specialists in the art, that typically, laundry powders themselves generate a relative humidity of about 40–45% at this temperature). After this time the solution properties of the powders were assessed as follows;

A concentrated solution in water of each powder was prepared (1 g in 20 ml) at ambient temperature (23° C.). The perfume performance of each powder was then assessed by a panel of trained assessors for perfume impact (on a 0–5 scale) and perfume quality at the following stages: from the dry powder, immediately after preparation of a solution of a powder, after 1.5 hours, 4 hours and overnight. The averaged impact results of the assessors are shown in FIG. 1. In FIG. 1, results for Powder A are shown by triangles, results for Powder B are shown by diamonds, results for Powder C are shown by empty squares and results for Powder D are shown by filled squares.

It can be seen from the graph of FIG. 1, that Powders A, B and D comprising particles in accordance with the invention clearly outperformed Powder C (without perfume particles) in the tests undertaken. Powders A, B and D demonstrated a strong orange note contribution (from encapsulated Perfume A) to their solution odour, whilst the odour from the solution of Powder C was that of Perfume B indicating that unprotected Perfume A had been almost entirely lost from Powder C because of its volatility.

In dry Powders A, B and D, Perfume A was not detectable (by odour) in any of the samples indicating that it was protected in the particles of the invention only being released upon contact with water.

Thus, the example demonstrates the improved perfume performance from particles in accordance with the invention during the soaking of clothes in a solution of laundry powder comprising said particles.

EXAMPLE 8

Improved Soak Performance with Particles Produced by the Dehydration Method

Particles prepared in accordance with Example 6 may be incorporated into a laundry powder which demonstrated an improved perfume performance during the soaking of clothes as indicated below.

The following additional laundry powder E was prepared by standard (non-tower) mixing techniques:

| | |
|---|---|
| Sodium tripolyphosphate | 40.00 |
| Sodium silicate | 6.20 |
| Sodium sulphate | 36.86 |
| SDBS* | 9.00 |
| $C_{12-15}$ alcohol (7EO) ethoxylate | 4.30 |
| CMC**, enzymes, fluorescer | 3.00 |
| Perfume B | 0.25 |
| Particles of Example 6 | 0.39 |

*Sodium dodecyl benzene sulphonate
**Sodium carboxymethyl cellulose

| Perfume B (all values are by wt %) | |
|---|---|
| Dodecanal | 0.25 |
| Methyl nonyl acetaldehyde | 0.50 |
| Allyl amyl glycollate | 1.50 |
| Anethole synthetic | 0.20 |
| Benzyl salicylate | 16.00 |
| Carvone laevo | 0.10 |
| Cedramber* | 4.40 |
| Cis-3 hexenyl salicylate | 0.50 |
| Citronellol | 2.50 |
| Coumarin | 1.00 |
| Damascone alpha | 0.20 |
| Dihydromyrcenol | 15.80 |
| Dipropylene glycol | 6.25 |
| Eugenol | 0.80 |
| Heliotropin | 0.70 |
| Hexyl cinnamic aldehyde | 13.00 |
| Lavandin abrialis | 0.70 |
| Lilial** | 8.00 |
| Linalool | 4.00 |
| Methyl dihydrojasmonate | 7.00 |
| Para-t-butyl cyclohexyl acetate | 6.00 |
| Patchouli acid washed | 0.40. |
| Tonalid*** | 9.00 |
| Undecalactone gamma | 1.20 |

*Trade mark of IFF
**Trade mark of Givaudan
***Trade mark of Bush Boake Allan

Powder E was then stored under "dry" conditions (as hereinabove described in Example 7) in standard packaging at 45° C. for one month, after which time its solution properties were assessed using the method described in Example 7 and compared with a sample of Powder C from Example 7. The averaged impact results of the assessors are shown in FIG. 2. In FIG. 2, results for Powder C are shown by empty squares and results for Powder E are shown by filled squares.

It can be seen from the graph of FIG. 2, that Powder E comprising particles in accordance with the invention, clearly outperformed Powder C (without perfume particles) in the tests carried out.

EXAMPLE 9

Extrusion Method 10.00 kg of a polymer slurry was prepared as described above under the heading "Preparation of Premixes A and B of Organic Polymer containing Absorbed Perfume" and pre-treated in the following manner to produce a more concentrated form of the polymer slurry. This was achieved by mixing the polymer slurry with an equal weight of water (i.e. 10.00 kg water) and then allowing the organic polymer beads to settle to the bottom of the mixing vessel. The excess water was then removed by decantation to produce a concentrated polymer slurry of 66.1% solids by weight.

To the concentrated polymer slurry (6.00 kg) was added Perfume A (3.97 kg) to produce Premix C. The premix was allowed to stand overnight to allow the perfume to be fully incorporated into the polymer. The resulting Premix C includes organic polymer and perfume in a 1:1 ratio.

6.28 kg of Premix C was then mixed with 6.25 kg of the maltose syrup, Flolys D5780 (ex Roquette Freres) to produce the desired mixture for extrusion in the form of a slurry. The mixture was then fed to, and extruded from, the extrusion apparatus described in Example 5, under the following conditions:

Stage 1 was held at 20° C.;
Stage 2 was held at 130° C.;
Stages 3–5 were held at 140° C.;
Stage 6 was held at 130° C.;
Stages 7–9 were held at 120° C.; and
Stage 10 was held at 100° C.

The mixture was pumped into the extruder at Stage 1. Stages 3 and 5 were vented to the atmosphere to allow removal of excess water. Additionally, a side feeder was provided at Stage 4 to provide additional venting to remove excess water. Stage 10, held at a temperature of 100° C., fed to a die with 4×1 mm holes (with screws run at 79 rpm and the back pressure at the die 45 bar). The resulting material comprising cores of organic polymer coated with molten sugar encapsulating material was face cut as it extruded from the die to produce uniform free-flowing granular particles of mean particle size ~1 mm, having a perfume content of 20.2%.

EXAMPLE 10

Extrusion Method

Premix D having a polymer to perfume ratio of 1:5 was prepared as described in Example 9 above. This was achieved by mixing 1.25 kg of Perfume A with 0.38 kg of the concentrated polymer slurry, followed by subsequent mixing of the premix with 0.63 kg of maltose syrup, Flolys D5780.

The extruded material comprising cores of organic polymer coated with molten sugar encapsulating material was produced using the same conditions for the extrusion apparatus as described in Example 9. The resulting particles were of similar appearance and behaviour to the particles of Example 9 and had a perfume content of 45.6%.

EXAMPLE 11

Extrusion Method

Particles in accordance with the invention were produced using the method of Example 9.

To a concentrated polymer slurry (1.54 kg), prepared as described in Example 9, was added Perfume A (1.00 kg) to produce Premix E. The premix was allowed to stand overnight to allow the perfume to be fully incorporated into the polymer. The resulting Premix E includes organic polymer and perfume in a 1:1 ratio.

To Premix E was then mixed maltose syrup (Flolys D5780) (0.625 kg) and maltodextrin (Glucidex 21, ex Roquette Freres) (0.50 kg) to produce the desired mixture for extrusion. The resulting mixture was then fed to, and extruded from, the extrusion apparatus described in Example 5, under the following conditions:

Stage 1 was held at 20° C.;
Stage 2 was held at 130° C.;
Stages 3–5 were held at 140° C.;
Stage 6 was held at 130° C.;
Stage 7–9 were held at 120° C.; and
Stage 10 was held at 100° C.

The mixture in the form of a slurry, was pumped into the extruder at Stage 1 at a speed of 5 kg/hr. Stages 3 and 5 were vented to the atmosphere to allow removal of excess water. Additionally, a side feeder was provided at Stage 4 to provide additional venting to remove excess water. Stage 10, held at a temperature of 100° C., fed to a die with 80×1 mm holes (win screws run at 79 rpm and the back pressure at the die 15 bar). The resulting material comprising cores of organic polymer coated with molten sugar encapsulating material was then fed to a spheroniser (ex Caleva). The resulting particles, having a perfume content of 21.1% and particle size of ~1 mm×3 mm, were uniform and free-flowing.

What is claimed is:

1. A particle suitable for inclusion in a dry product or article, comprising:

a core of non-porous swellable material containing perfume absorbed therein, the core being coated with at least one water-soluble encapsulating material which is impervious to the said perfume, the water-soluble encapsulating material dissolving completely in water or aqueous solutions at 40° C., wherein the core material is a polymer of a vinyl monomer.

2. A particle according to claim 1, wherein the polymer is a polymer of one or more monomers which are acrylic and/or alkyl acrylic esters of formula:

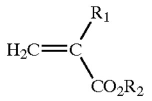

wherein $R_1$ is hydrogen or straight or branched alkyl of 1 to 6 carbon atoms and $R_2$ is straight or branched alkyl of 1 to 8 carbon atoms.

3. A particle according to claim 1, wherein the polymer is a polymer of one or more monomers which are acrylic or methacrylic esters of formula:

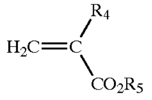

where $R_4$ is hydrogen or methyl and $R_5$ is a straight or branched alkyl of 9 to 16 carbon atoms.

4. A particle according to claim 2 or claim 3, wherein the organic polymer is cross-linked with a cross-linkable monomer having at least two carbon-carbon double bonds.

5. A particle according to claim 1, wherein the particle additionally comprises at the exterior of the core, a further polymer which incorporates free hydroxyl groups.

6. A particle according to claim 5, wherein said further polymer is selected from polyvinyl alcohol, cellulose, or chemically modified cellulose.

7. A particle according to claim 6, wherein the water-soluble encapsulating material is selected from hydroxylic compounds, proteins and synthetic film-forming polymers, or mixtures thereof.

8. A particle according to claim 7, wherein the hydroxylic compounds are selected from one or more of: carbohydrates or derivatives thereof, and natural or synthetic gums, or mixtures thereof.

9. A particle according to claim 8, wherein the encapsulating material forms a glassy coating.

10. A particle according to claim 9, wherein the w/w ratio of core material to perfume is in the range 5:1 to 1:5.

11. A particle according to claim 10, wherein the w/w ratio of core material to perfume is in the range 3:1 to 1:5.

12. A particle according to claim 11, wherein the particles are stable at 20° C. and at least 40% relative humidity.

13. A dry product or article containing a particle according to claim 1 or claim 12.

14. A product or article according to claim 13, selected from the group consisting of laundry products, autodishwash powders, autodishwash tablets, sheet conditioners, rim blocks, soap, and powder and granular cleaning compositions.

* * * * *